United States Patent
Hahn (10) Patent No.: US 6,675,131 B2
(45) Date of Patent: Jan. 6, 2004

(54) METHOD OF DEALING WITH PROBLEMS AFFECTING A MEDICAL APPARATUS AND A MEDICAL APPARATUS SUITABLE FOR CARRYING OUT SUCH A METHOD

(75) Inventor: Guenter Hahn, Shanghai (CN)

(73) Assignee: Siemens Aktiengesellschaft, Munich (DE)

( * ) Notice: Subject to any disclaimer, the term of this patent is extended or adjusted under 35 U.S.C. 154(b) by 187 days.

(21) Appl. No.: 09/960,385

(22) Filed: Sep. 24, 2001

(65) Prior Publication Data
US 2002/0042717 A1 Apr. 11, 2002

(30) Foreign Application Priority Data

Sep. 22, 2000 (DE) .......................... 100 47 547

(51) Int. Cl.⁷ ................................. G06F 9/00
(52) U.S. Cl. ...................... 702/188; 702/184; 702/185; 702/186; 702/187
(58) Field of Search ................ 702/182–188; 340/3.1, 525; 700/17

(56) References Cited

U.S. PATENT DOCUMENTS

| | | |
|---|---|---|
| 5,778,791 A | 7/1998 | Albus et al. |
| 6,122,565 A | 9/2000 | Wenning et al. |
| 6,442,433 B1 * | 8/2002 | Linberg ........................ 607/60 |
| 6,480,762 B1 * | 11/2002 | Uchikubo et al. .......... 700/253 |
| 2002/0065775 A1 * | 5/2002 | Monaghan .................... 705/43 |
| 2003/0023325 A1 * | 1/2003 | Adachi et al. ................. 700/9 |

FOREIGN PATENT DOCUMENTS

| | | |
|---|---|---|
| DE | 36 09 927 | 10/1987 |
| DE | 195 05692 | 8/1996 |
| DE | 196 50569 | 6/1998 |
| DE | 197 49002 | 8/1998 |
| WO | WO 87/06045 | 10/1987 |
| WO | WO 98/25396 | 6/1998 |

* cited by examiner

Primary Examiner—Marc S. Hoff
Assistant Examiner—Felix Suarez
(74) Attorney, Agent, or Firm—Young & Thompson (57) ABSTRACT

The invention relates to dealing with problems affecting a medical apparatus. In this method, if a problem occurs, a service center is notified of the problem by telecommunication, whereupon the service center issues problem-specific instructions by telecommunication for determining data with respect to the notified problem. Then, on the basis of the determined data, of which it has been notified by telecommunication, the service center determines a measure for dealing with the problem and gives notice of it by telecommunication, whereupon the measure for dealing with the problem is taken and a test of the medical apparatus is performed.

11 Claims, 6 Drawing Sheets

METHOD OF DEALING WITH PROBLEMS AFFECTING A MEDICAL APPARATUS AND A MEDICAL APPARATUS SUITABLE FOR CARRYING OUT SUCH A METHOD

A method of dealing with problems affecting a medical apparatus and a medical apparatus suitable for carrying out such a method.

The invention relates to a method of dealing with problems affecting a medical apparatus and to a medical apparatus suitable for carrying out such a method.

For medical apparatuses that are currently commercially available there are generally methods of dealing with problems. To carry out these methods, the apparatuses have comprehensive self-test programs, which in some circumstances can be activated or interrogated by telecommunication or remote access means. Extensive service documents are also usually available.

However, appropriately trained (service) personnel are usually required for carrying out methods of the type stated at the beginning in order to allow the means of assistance respectively available for dealing with problems to be correctly applied, the test results to be evaluated and defective parts to be repaired or exchanged.

The invention is based on the object of designing a method of the type stated at the beginning in such a way that the training measures required for carrying out the method can be less expensive. The invention is also based on the object of specifying a medical apparatus suitable for carrying out such a method.

According to the invention, the object concerning a method is achieved by a method of dealing with problems affecting a medical apparatus, with the following method steps:

when a problem affecting the medical apparatus occurs, a service center is notified of the problem by telecommunication, problem-specific instructions for determining data on the medical apparatus with respect to the notified problem are issued by the service center by telecommunication, data on the medical apparatus corresponding to the instructions issued are obtained and notified to the service center by telecommunication, in accordance with the data notified, a measure for dealing with the problem is determined by the service center and notified by telecommunication, and the measure for dealing with the problem is taken.

It is consequently clear that, using the capabilities of telecommunication, even an apparatus user who is not specially trained, for example a physician or a medical assistant, is enabled by the method according to the invention to act on dealing with the problem by following instructions from the service center. This applies in particular if, according to one variant of the invention, the apparatus user carrying out the method is given information assisting him in carrying out the method when performing at least one of the method steps according to claim 1.

According to variants of the invention, a setting operation is performed and/or an exchange of a component is made as a measure for dealing with a problem, with a preferred embodiment of the invention providing that a component to be exchanged is ordered by telecommunication.

According to one variant of the invention, the success of the measures taken for dealing with problems is checked by performing a test on the medical apparatus after a measure for dealing with a problem has been taken, the service center being notified of the test result by telecommunication, at least if it is negative.

The object concerning a medical apparatus is achieved according to the invention by a medical apparatus which contains a data memory in which information serving to assist in the performance of at least one of the method steps according to claim 1 is stored and, depending on the problem, is fed by the data memory to a display device.

To avoid errors in the exchange of components which can be exchanged as part of a measure for dealing with a problem, that is components which the apparatus user is permitted to exchange, it is provided according to variants of the invention that such components are designed in a way ensuring that they cannot be mixed up or the connections of such components serving for power and/or signal transmission are designed in a way ensuring that they cannot be mixed up.

The exchange of components which can be exchanged as part of a measure for dealing with a problem becomes particularly simple and reliable if, according to one variant of the invention, such components are provided with a visible code, which is displayed as information serving to assist in the performance of at least one of the method steps according to claim 1 if a component is to be exchanged.

The telecommunication with the service center becomes particularly simple if the medical apparatus has telecommunication means which connect it to the service center. This avoids the necessity in the case of separate telecommunication means for data and information to be transmitted over external lines and the like between the medical apparatus and the telecommunication means.

An exemplary embodiment of the invention is represented in the attached schematic drawings, in which.

Figure 1:
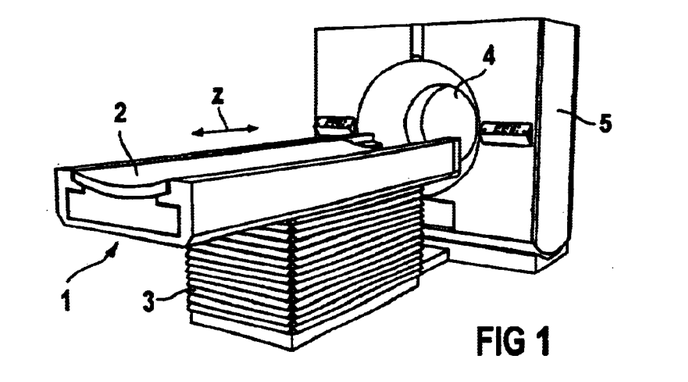
FIG. 1 shows a CT apparatus according to the invention, suitable for carrying out the method according to the invention, in a perspective representation.

Represented in FIG. 1 is a medical apparatus according to the invention, the apparatus concerned being a CT apparatus which has a patient-supporting table 1 with a supporting plate 2, which can be displaced in the direction of the double-headed arrow z, in the direction of its longitudinal axis parallel to the system axis of the CT apparatus and which, in the case of the exemplary embodiment described, is attached on a base 3 in a vertically adjustable manner, but alternatively may also be attached in a fixed manner.

An object under investigation lying on the supporting plate 2, for example a patient 11 (see FIG. 2), can be positioned into the measuring opening 4 of a measuring unit 5 by a corresponding longitudinal displacement of the supporting plate 2.

Figure 2:
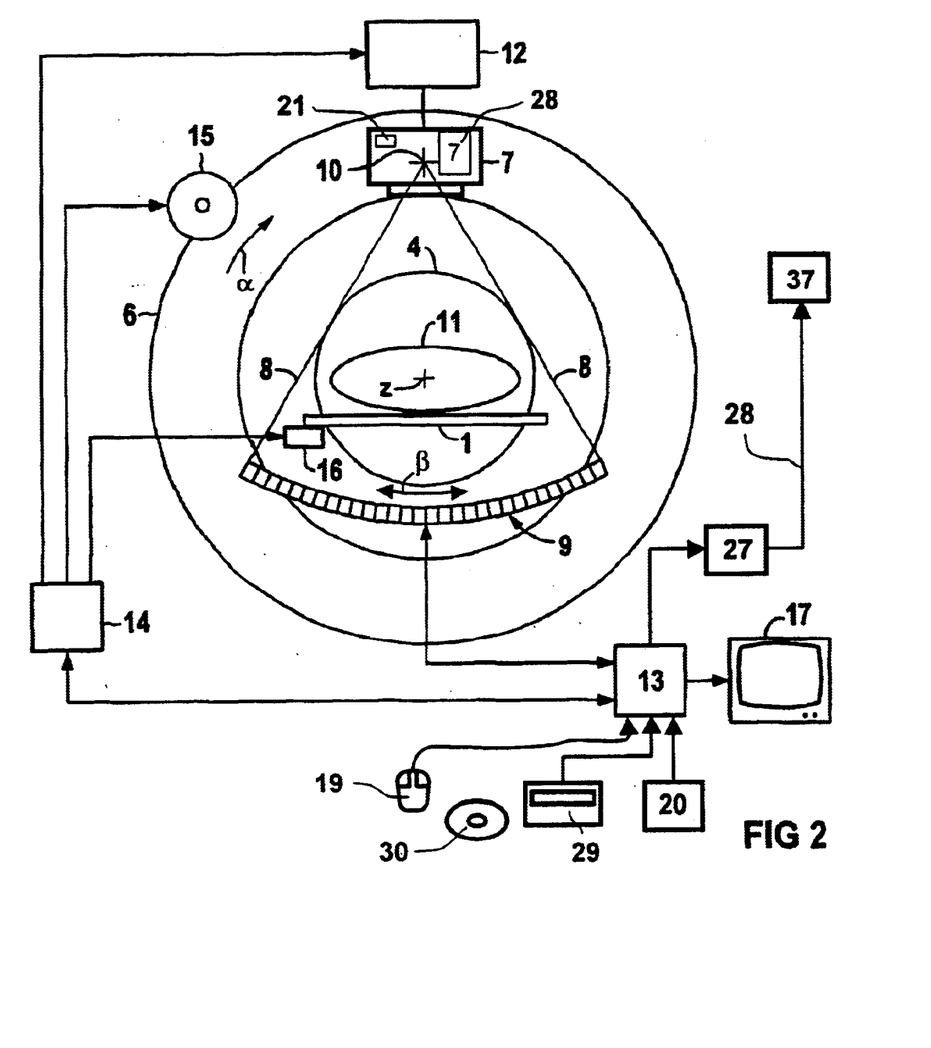
FIG. 2 shows the CT apparatus according to FIG. 1 in a schematic, partially block-diagram-like representation.

As can be seen from FIG. 2, the measuring unit includes a ring mount 6 which surrounds the measuring opening 4 and on which an X-ray radiation source 7 and a detector system 9 are arranged lying opposite each other, the detector system in the case of the exemplary embodiment described being formed by a row of, for example, 512 detector elements curved in the form of an arc of a circle, each detector element being assigned a channel angle $\beta\beta$.

The X-ray radiation source 7 has a focus, denoted by 10, from which there emerges a fan-shaped X-ray radiation beam 8 impinging on the detector system 9.

Connected to an electronic computing device 13 is a display device 17, provided for the display of section images. Also connected to the electronic computing device 13 is an input instrument, in the case of the exemplary embodiment represented a mouse 19, which allows the CT apparatus to be operated on the basis of graphic operator-control menus which can be presented on the display device 17.

For controlling the rotary movement of the ring mount 6, the longitudinal movement of the supporting plate 2 and the X-ray radiation source 7, a control unit 14 is provided, activating the drives 15 and 16 assigned to the ring mount and the supporting plate 2 and also activating the high-voltage generator 12.

For scanning a patient 11 lying on the supporting plate 2, the ring mount 6 is turned in the $\alpha\alpha$ direction about the system axis z running centrally through the measuring opening 4 and at right angles to the plane of the drawing of FIG. 2, to be precise in such a way that the focus 10 of the X-ray radiation source 7 moves on a circular path which lies in a plane at right angles to the system axis. As this happens, the fan-shaped X-ray radiation beam 8 emerging from the X-ray radiation source 7 fed by a high-voltage generator 12 irradiates a planar layer of the patient 11 running at right angles to the system axis 2.

At predetermined angular positions, known as the projection angles $\alpha\alpha$, the output signals of the detector elements of the detector system 9 corresponding to the corresponding projections are fed to the electronic computing device 13, which computes from these the attenuation values belonging to the individual detector elements, and consequently channel angles $\beta\beta$, of the layer of the patient detected by the X-ray radiation beam 8.

Since the supporting plate 2 is displaceable in the direction of the system axis z, a volume of the patient 11 can be scanned by either the supporting plate 2 being continuously displaced during continuous rotation of the measuring unit 5 (known as spiral scanning) or by the supporting plate 2 being displaced step by step in such a way that a number of parallel layers, preferably adjacent to one another, are scanned one after the other (known as sequence scanning). The sets of attenuation values corresponding to the projections thereby recorded are fed to the electronic computing device 13, which determines section images from these sets of values on the basis of reconstruction algorithms known per se and, as mentioned, displays them on the display device 17.

In the case of a problem occurring during the operation of the CT apparatus, for example a defect, an operating fault or a malfunction, the electronic computing device 13 also performs the function of determining this problem and displaying it on the display device 17.

Figure 4:
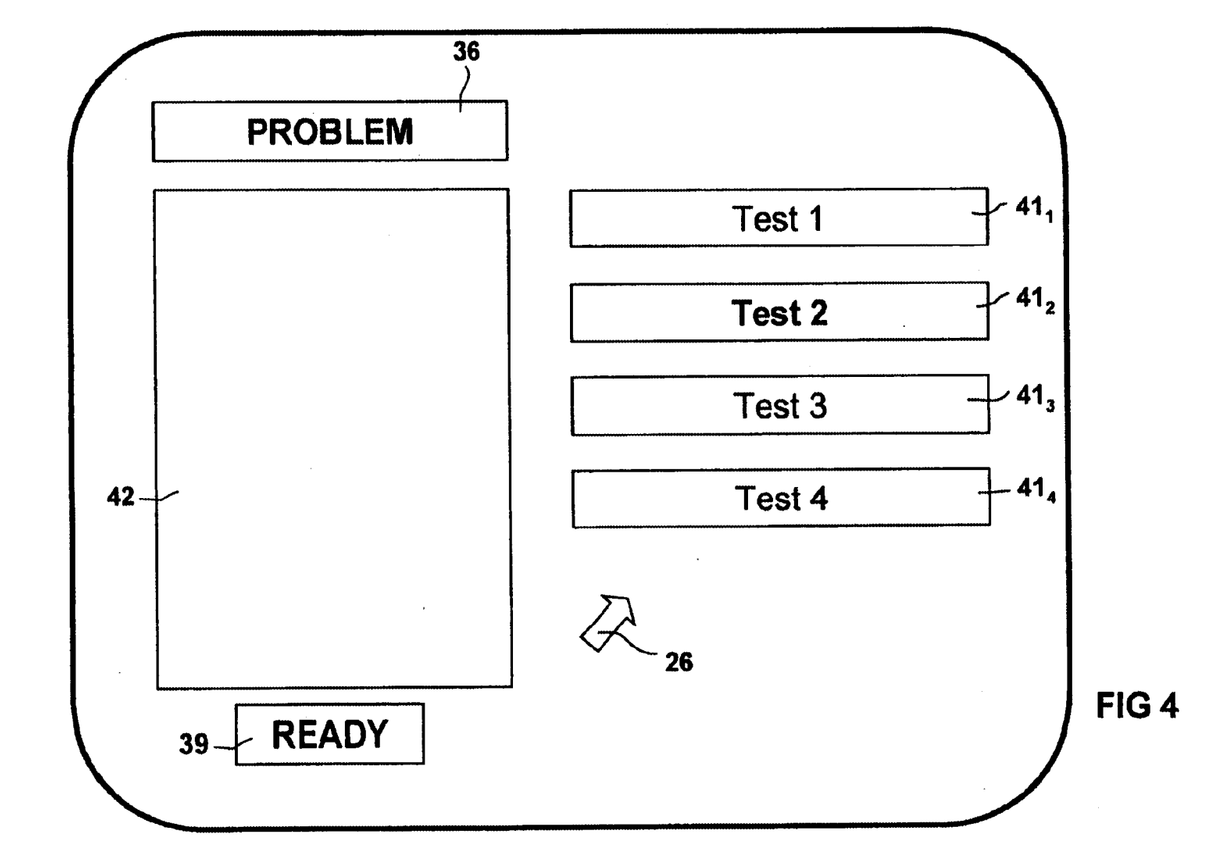
FIGS. 4 to 7 show a display occurring during the operation of the CT apparatus according to the invention.

For the purposes mentioned, connected to the electronic computing device 13 is a data memory 20, in which there is stored, inter alia, a diagnostic program, which enables the electronic computing device 13 to identify certain problems and display them in a corresponding text zone 36 on a screen mask which is illustrated in FIG. 4 and which the electronic computing device 13 displays if a problem occurs. In this case, the electronic computing device 13 cannot identify all problems, only those which the diagnostic program is designed to identify.

Figure 3:
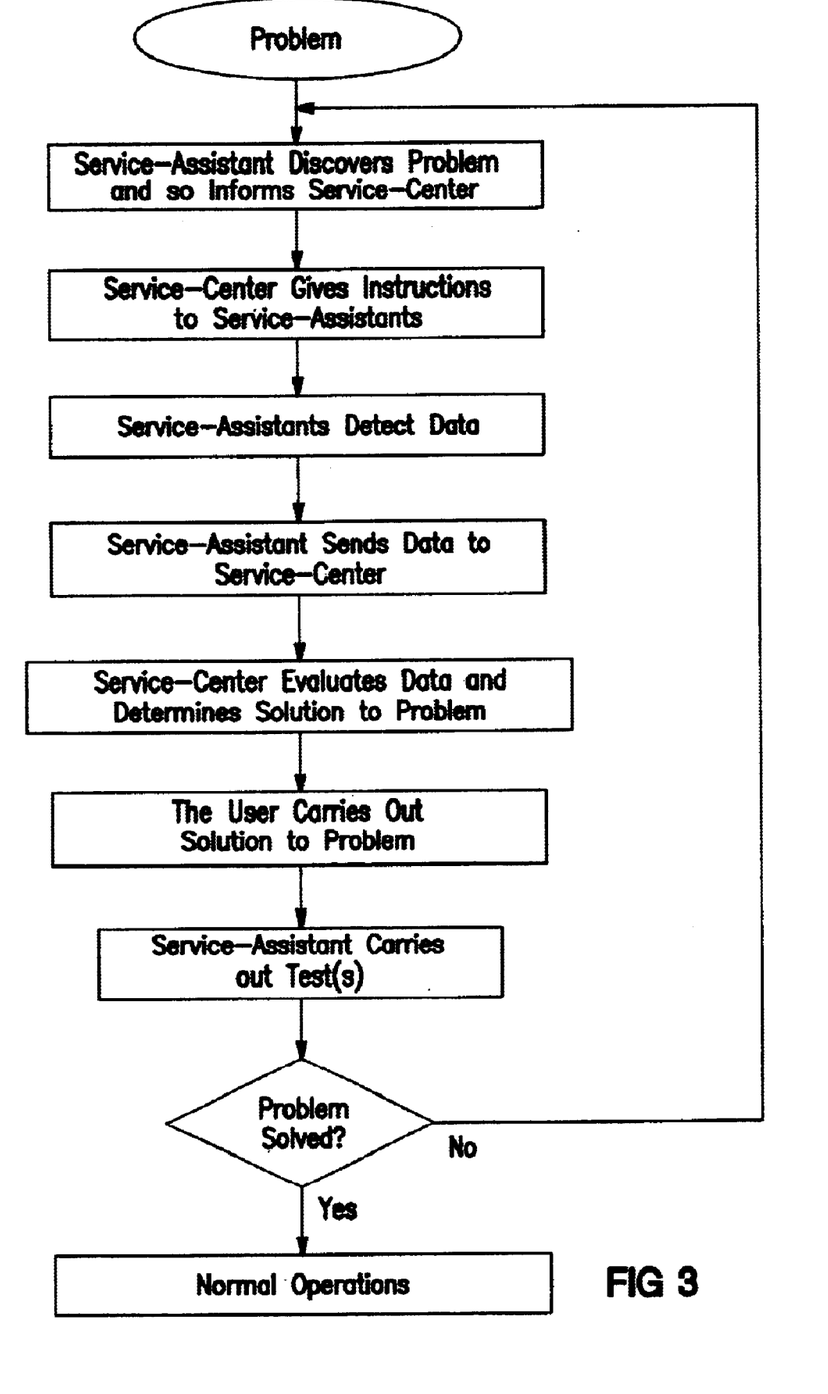
FIG. 3 shows a flow diagram illustrating the sequence of the method according to the invention.

Part of the diagnostic program is a subroutine, referred to hereafter as the service assistant, the mode of operation of which is illustrated in FIG. 3 and which enables the apparatus user to make contact with a service center 37 of the manufacturer of the CT apparatus by way of telecommunication if a problem occurs.

For this purpose, connected to the electronic computing device 13 are telecommunication means, which in the case of the exemplary embodiment described take the form of a modem 27 connected by a data line leading to the service center 37, for example a telephone line 28.

If reference is made hereafter to the service assistant performing certain steps, this is to be understood as meaning that the electronic computing device 13 instigates the corresponding steps by executing said subroutine.

Once the service assistant has identified a problem which has occurred, and has displayed it in the text zone 36, there is the possibility of notifying the service center 37 of the problem which has occurred via the modem 27 and the telephone line 28 by positioning the mouse pointer 26 on the text zone 36 and double clicking.

If a message concerning a problem which has occurred reaches the service center 37, it analyzes the problem and sends instructions specifying one or more tests to be carried out to the service assistant via the telephone line 28 and the modem 27. These tests, four in the case of the exemplary embodiment described, and denoted in FIG. 4 by Test 1 to Test 4, are displayed in text zones $40_1$ to $40_4$, the test respectively to be performed next being optically highlighted and able to be activated in the way described in conjunction with the notification of the problem by means of the mouse pointer 26.

An activated test is carried out by the service assistant, which sends the data obtained thereby to the service center 37 via the modem 27 and the telephone line 28. In the case of the situation illustrated in FIG. 4, four tests are to be carried out, Test 1 already having been carried out and the next test to be carried out being Test 2, which is illustrated in FIG. 4 by bold script. If the apparatus user has to be active during a test, for example take a test exposure, the service assistant gives him corresponding instructions in a suggestions zone 42. Once the user has followed the respective instructions, he notifies the service assistant of this by actuating a button 39 designated READY, whereupon the service assistant continues with its activity.

Once all the tests to be carried out have taken place, the data transmitted by the service assistant to the service center 37 are analyzed there, measures for dealing with a problem are determined and the service assistant is notified of these measures for dealing with the problem via the telephone line 28 and the modem 27.

Figure 5:
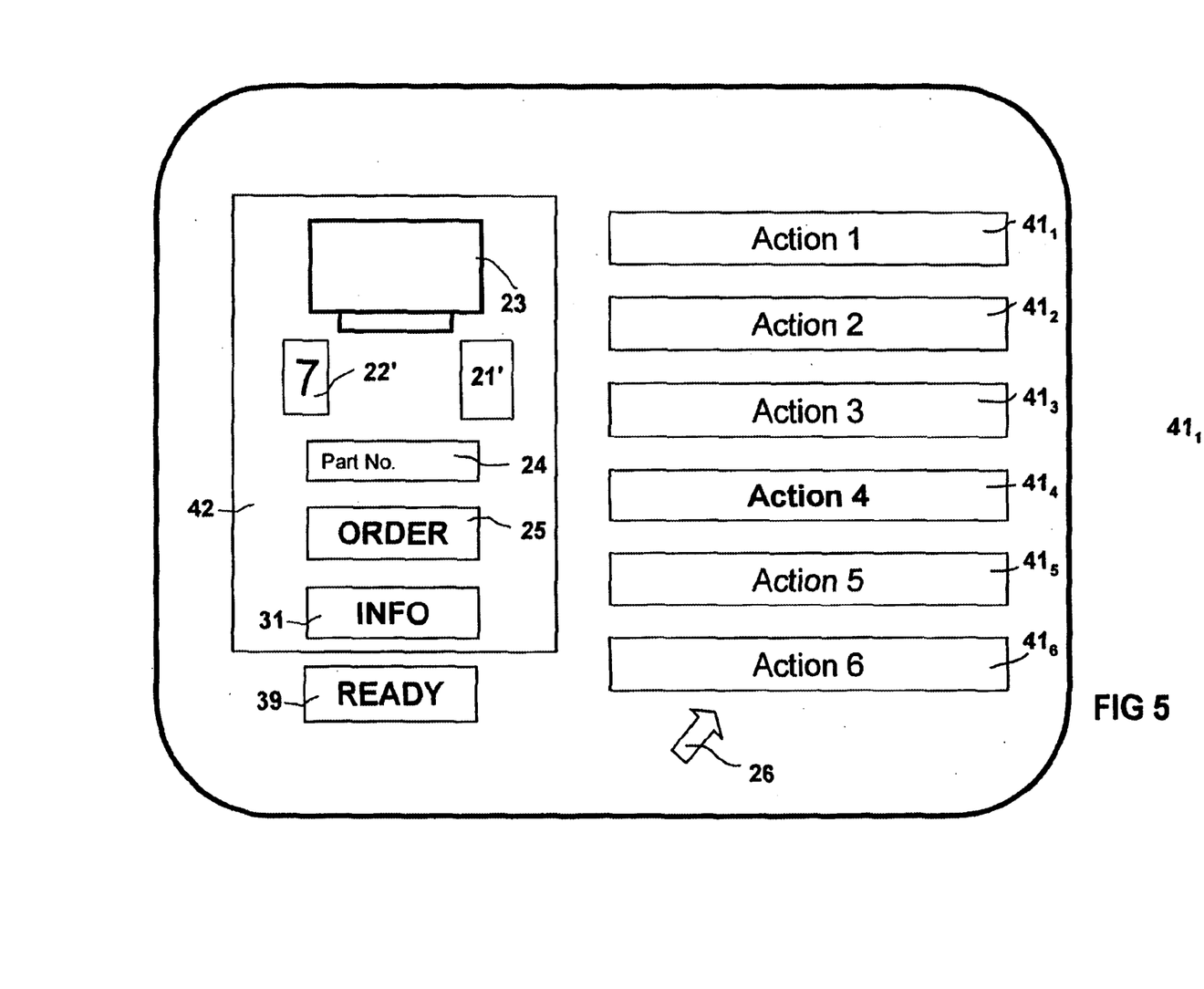

Said service assistant then displays the screen mask represented in FIG. 5 on the display device 17 and, in the case of the exemplary embodiment described, displays six measures determined by the service center 27, which are denoted by Action 1 to Action 6, in text zones $41_1$ to $41_6$, it again being the case here that the measure to be carried out next is optically highlighted. In the case of the situation represented in FIG. 4, this is the measure 4, which is illustrated by bold script.

In the suggestions zone 42, provided as in the screen mask according to FIG. 4, the service assistant displays suggestions for carrying out the measure concerned at the particular time.

Figure 6:
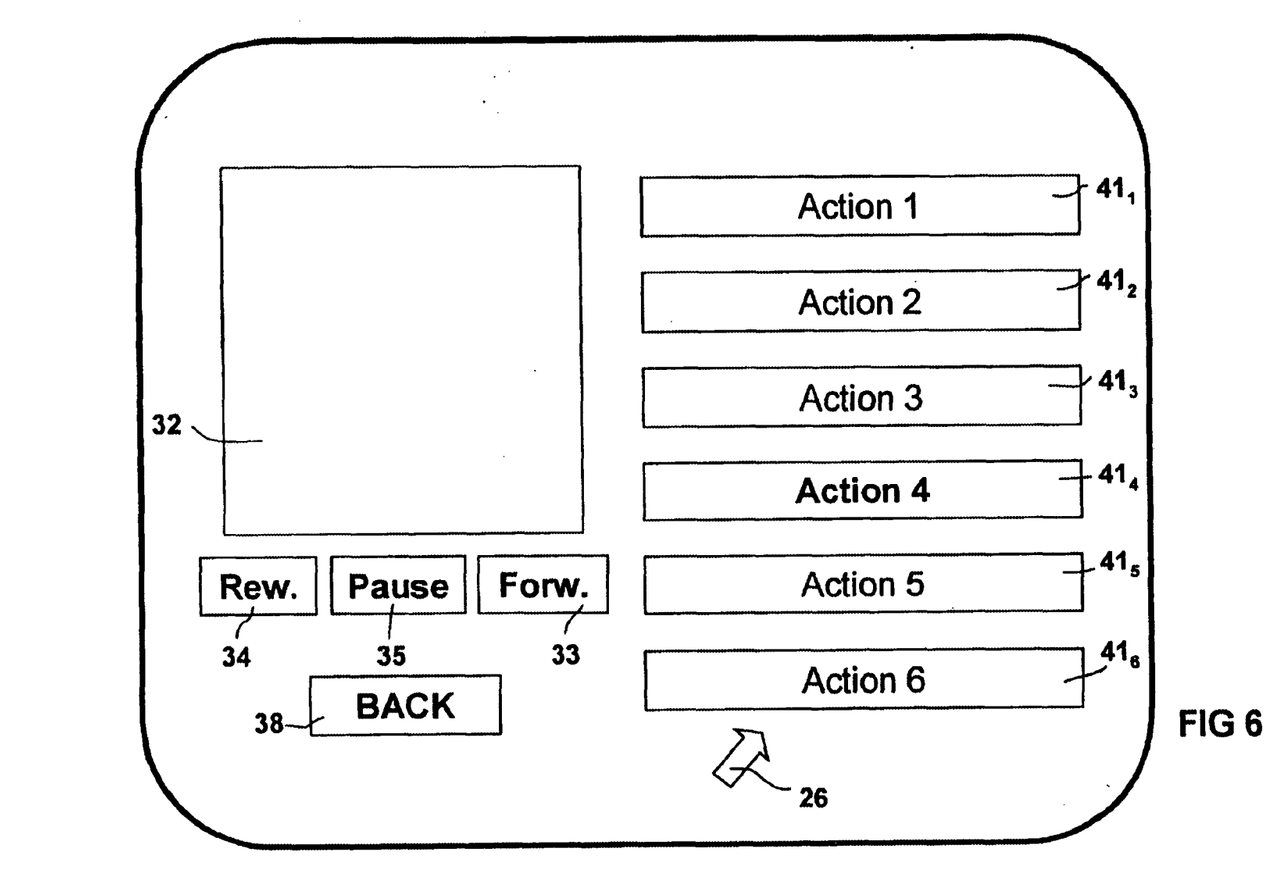

If further information is available with respect to the measure concerned at the time, the service assistant displays in the suggestions zone 42 a button 31 designated INFO, which, when actuated, causes the service assistant to change to a further screen mask, which is represented in FIG. 6 and will be described later in more detail.

Once carrying out of the measure in question has been completed, the apparatus user actuates a button 39 provided with the designation READY, whereupon the service assistant optically highlights the measure to be carried out next.

Figure 7:
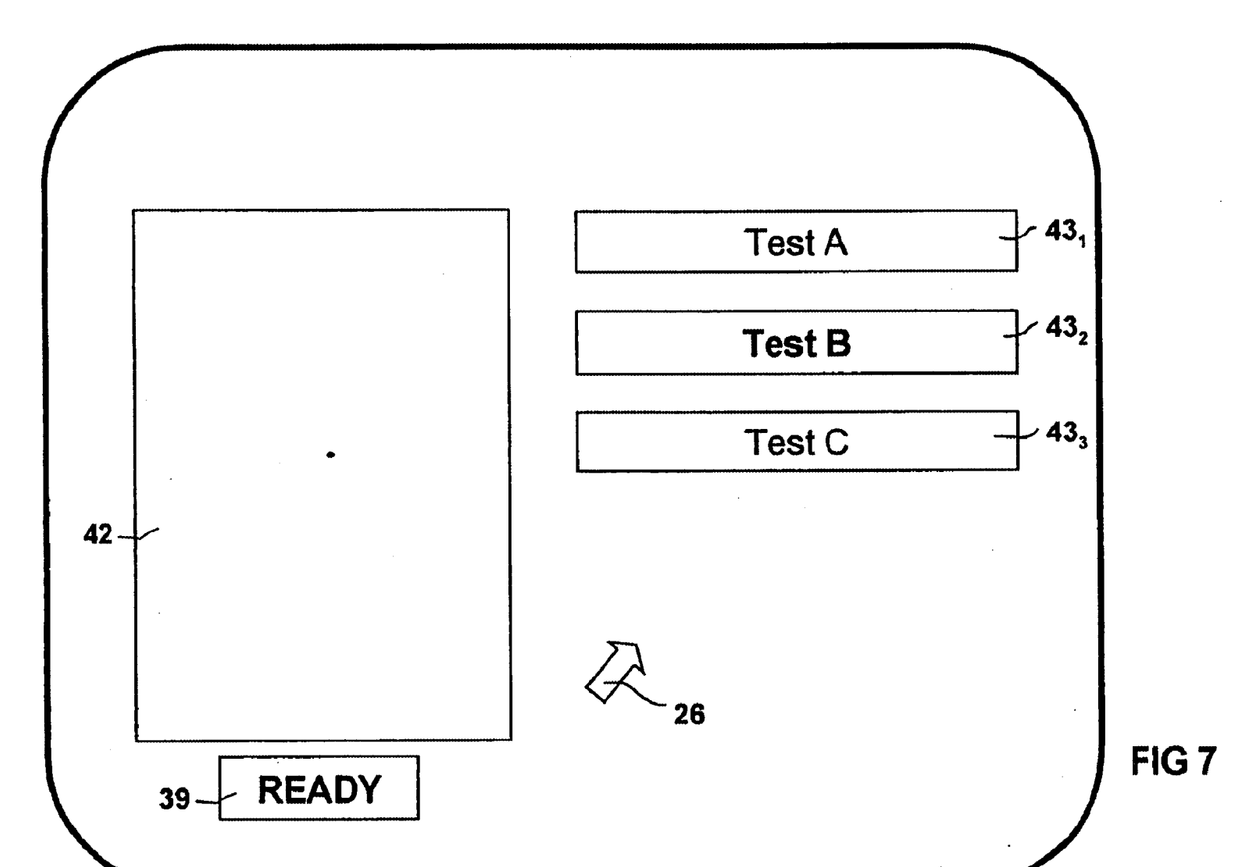

Dependent on the respective problem, after individual measures and/or after the completion of groups of measures and/or after the completion of all the measures, the service assistant changes to the screen mask represented in FIG. 7, which is constructed in a similar way to the screen mask according to FIG. 4, and displays in text zones $43_1$ to $43_3$ tests respectively to be carried out, three in the case of the exemplary embodiment described, and denoted by Test A to Test C, with Test B being the test to be carried out at the time in the case of FIG. 4.

In response to actuation of the button corresponding to the test to be carried out at the time, the service assistant then carries out the respective test, the details specified in connection with FIG. 4 applying analogously.

Depending on the problem, the information required for carrying out tests is either stored in the data memory 20 or is notified to the electronic computing device 13 together with the measures to be carried out for dealing with the problem.

If all the tests proceed positively, the service assistant ends its activity, i.e. the CT apparatus reverts to its normal operation and the electronic computing device 13 again displays on the display device 17 a screen mask with a menu serving for the operator control of the CT apparatus. If one of the tests proceeds negatively, the service assistant displays a request to make contact with service personnel of the apparatus manufacturer, the possibility of contacting the service personnel via the modem 27 being provided by actuating a corresponding button which is not represented.

Some of the components of the CT apparatus according to the invention are known as self-change components, i.e. components which can be exchanged by the apparatus user himself during a measure for dealing with a problem, without any need to call on the assistance of specially trained service personnel. In the case of the exemplary embodiment described, such components are the X-ray radiation source 7, the detector system 9, the high-voltage generator 12 and air filters not represented in the figures. As shown in FIG. 2 only for the X-ray radiation source 7, for reasons of overall clarity, the self-change components are provided with a color and number code, i.e. each self-change component has a color zone 21 and an inscription zone 22, as illustrated in the case of the X-ray radiation source 7, the color code being applied in the respective color zone and the number code being applied in the respective inscription zone. In the case of the X-ray radiation source 7 in the present exemplary embodiment, the number code applied in the inscription zone 22 of the X-ray radiation source 7 coincides with the reference number of the X-ray radiation source 7.

The color and number codes belonging to the individual self-change components and icon-like illustrations of the self-change components are likewise stored in the data memory 20.

If one of the self-change components is to be exchanged as a measure for solving a problem in the case of the CT apparatus according to the invention, the service assistant displays the respective self-change components in the suggestions zone 42 in the screen mask represented in FIG. 5, with FIG. 4 representing the situation in the case in which the X-ray radiation source 7 is the self-change component to be exchanged.

Accordingly, the service assistant displays in accordance with the color and number code of the X-ray radiation source 7 this color and number code in a color zone 21' and an inscription zone 22'. Furthermore, the service assistant displays the icon 23 illustrating the X-ray radiation source 7.

In addition, the service assistant displays a text zone 24, with the part number of the respective self-change component, likewise stored in the data memory 20, and a button 25 provided in FIG. 3 with the designation ORDER.

If the mouse pointer 26 is moved onto the button 25 and is double clicked, the service assistant orders the required self-change component, that is in the present case the X-ray radiation source 7, from the manufacturer of the CT apparatus via the modem 27, and for this purpose transmits to the manufacturer of the CT apparatus in addition to the part number all the data necessary for executing the order, such as for example the location of the CT apparatus, customer number, etc. The service assistant likewise takes these data from the data memory 20, in which these data are also stored.

When the self-change component arrives, the apparatus user can call up information on the installation of the respective self-change component by actuating the button 31 designated INFO and double clicking it. In the case of the exemplary embodiment represented, the service assistant then accesses a CD-ROM drive 29, in which a CD-ROM 30 containing the corresponding information is located, this information being presented by the service assistant on the screen of the display device 17 in a display zone 32 in a screen mask illustrated in FIG. 6.

The information stored on the CD-ROM 30 takes the form of exploded drawings and/or series of drawings or photographs and/or video sequences.

The information presented in the display zone 32 allows the apparatus user to navigate by means of three buttons 33 to 35, moving forward in the information with the button 33 designated Forw. and moving backward by means of the button 34 designated Rew. The button 35 designated Pause serves in the case where video sequences are displayed for presenting a specific image of the video sequence as a still picture.

Once the exchange of the respective self-change component has taken place, the apparatus user returns to the screen mask represented in FIG. 5 by actuating a button 38 designated BACK and actuates the button 39 designated READY.

The service assistant then changes to the screen mask represented in FIG. 7 and displays the tests to be carried out.

As mentioned, in the case of a positive test outcome, the CT apparatus changes back to its normal operation. In the case of a negative test outcome, the service assistant, as mentioned, displays a request to make contact with service personnel of the apparatus manufacturer, the possibility of contacting the service personnel via the modem 27 being provided by actuating a corresponding button.

In the case of the exemplary embodiment described, the data memory 20 and the modem 27 and the CD-ROM drive 29 are represented as separate components. These may, however, also be integrated into the electronic computing device 13.

In the case of the exemplary embodiment described, the self-change components are provided with a color and number code, but it is also possible for only a color code or only a number code to be provided. Furthermore, a letter code may be provided instead of the number code.

In the case of the exemplary embodiment described, the data traffic between the modem 27 and the manufacturer of the CT apparatus takes place in a wire-bound manner over the telephone network. Instead of this, the connection may also take place wirelessly over a mobile radio network. Furthermore, in the case of the data exchange between the CT apparatus and the manufacturer of the CT apparatus, the possibilities of remote data transmission, the Internet, in particular the World Wide Web, and also e-mail can be utilized.

A problem in which the exchange of only one self-change component is required is described above. Depending on the problem occurring, it may also be possible, however, to exchange a number of self-change components, the electronic computing device 13 additionally presenting the corresponding data and information on the display device 17.

As a departure from the above procedure for ordering a self-change component to be exchanged, it may also be envisaged that it is sufficient to click on the icon representing it to send the order. It is then possible to dispense with the button 25.

The screen masks of the service assistant represented in connection with the above exemplary embodiment are to be understood as being given only by way of example.

To rule out errors in the case of exchanging self-change components, they, and similarly their connections serving for power and/or signal transmission, are designed in a way not represented in the FIGS. such that they cannot be mixed up, so that neither self-change components can be inadvertently mixed up, that is for example an X-ray radiation source cannot be fitted instead of a detector, nor can the connections be mixed up, that is the connection of the X-ray radiation source cannot be fitted at the connection of the CT apparatus intended for the detector.

To be specific, the risk of mix-ups can be reduced by

- self-change components having as small a number of connections as possible,
- different self-change components having different types of connection,
- the lengths of cables provided on connections of self-change components being dimensioned such that the cable length is just sufficient when the self-change component is installed,
- the connections also being provided with color codes and/or special graphic symbols and/or stickers.

If it is nevertheless still possible for connections to be mixed up, the existence of a mix-up is established and reported during the course of the tests taking place after a self-change component has been exchanged, so that no damage can occur.

Installation and removal of self-change components is made easier by the following measures, which are not represented:

- guiding and pre-adjusting pins are provided for the self-change components,
- the self-change components and the CT apparatus are designed such that no mechanical adjustment is required when self-change components, such as for example a detector and X-ray radiation source, are exchanged, and transport cases in which the self-change components assume such a position that they can be pushed out of the transport cases onto the guiding and pre-adjusting pins without any problem are used for the self-change components.

The risk of accidents during the installation and removal of self-change components is reduced by the self-change components being arranged under covers in a way not represented. The outer covers of the CT apparatus can only be opened with the aid of special tools and only about five minutes after the CT apparatus has been switched off, in order to protect the apparatus user from high voltage. When the cover has been opened, the CT apparatus can only be switched on with a special key.

Moreover, it may be provided that the CT apparatus automatically detects and remembers the necessity for changing or supplying consumable material, such as for example the necessary exchange of filters or of the X-ray radiation source.

The invention is described above by the example of a CT apparatus; it may, however, be used in the case of any other medical apparatuses.

To sum up, the following can be stated with respect to the invention:

The way in which problems are dealt with, i.e. the entire fault-determining and service procedure, is devised for apparatus users without any special training.

A service assistant (comparable with set-up programs for PC standard software) assists and accompanies the apparatus user during the entire procedure of dealing with a problem. The apparatus user operates the apparatus and gathers the data required for investigating the respective problem, while qualified personnel evaluate the results/data at the service center and on this basis work out proposals for dealing with a problem, i.e. for example rectifying faults, and notify the apparatus user of them. The service assistant is a piece of self-explanatory software which tells the apparatus user precisely what he has to do and which includes a special diagnostic process for all major and frequently occurring problems. Problems for which the service assistant does not include a diagnostic process cannot be dealt with by the apparatus user, which means that, to eliminate the problem, the entire apparatus must be exchanged or trained service personal must tackle the problem on site.

If need be, the apparatus user can exchange the special self-change components without special training or outside assistance. This involves taking measures which make it possible for such self-change components to be exchanged by the apparatus user without having to fear that the apparatus may be damaged.

What is claimed is:

1. A method of dealing with problems affecting a medical apparatus, with the following method steps:

when a problem affecting the medical apparatus occurs, a service center is notified of the problem by telecommunication, problem-specific instructions for determining data on the medical apparatus with respect to the notified problem are issued by the service center by telecommunication, data on the medical apparatus corresponding to the problem-specific instructions issued are obtained and notified to the service center by telecommunication, in accordance with the data notified, a measure for dealing with the problem is determined by the service center and notified by telecommunication, and the measure for dealing with the problem is taken.

2. The method as claimed in claim 1, in which an apparatus user carrying out the method is given information assisting him in carrying out the method when performing at least one of the method steps according to claim 1.

3. The method as claimed in claim 1, in which a test on the medical apparatus is performed after a measure for dealing with a problem has been taken, the service center being notified of the test result by telecommunication, at least if it is negative.

4. The method as claimed in claim 1, in which a setting operation is performed as the measure for dealing with a problem.

5. The method as claimed in claim 1, in which an exchange of a component is made as the measure for dealing with a problem.

6. The method as claimed in claim 5, in which a component to be exchanged is ordered by telecommunication.

7. A medical apparatus for carrying out the method as claimed in claim 1, the medical apparatus containing a data memory in which information serving to assist in the performance of at least one of the method steps according to claim 1 is stored and, depending on the problem, is fed by the data memory to a display device.

8. The medical apparatus as claimed in claim 7, in which components to be exchanged as part of a measure for dealing with a problem are designed in a way ensuring that they cannot be mixed up.

9. The medical apparatus as claimed in claim 7, in which connections serving for power and/or signal transmission of components which can be exchanged as part of a measure for dealing with a problem are designed in a way ensuring that they cannot be mixed up.

10. The medical apparatus as claimed in claim 7, components of which can be exchanged as part of a measure for dealing with a problem are provided with a visible code which is displayed as information.

11. The medical apparatus as claimed in claim 7, which has telecommunication means connecting the medical apparatus to the service center.

* * * * *